(12) United States Patent
Kiyotomo et al.

(10) Patent No.: US 12,239,541 B2
(45) Date of Patent: Mar. 4, 2025

(54) ARTIFICIAL KNEE JOINT

(71) Applicant: TEIJIN NAKASHIMA MEDICAL CO., LTD., Okayama (JP)

(72) Inventors: Dai Kiyotomo, Okayama (JP); Takayuki Inoue, Okayama (JP)

(73) Assignee: TEIJIN NAKASHIMA MEDICAL CO., LTD., Okayama (JP)

( * ) Notice: Subject to any disclaimer, the term of this patent is extended or adjusted under 35 U.S.C. 154(b) by 818 days.

(21) Appl. No.: 17/602,648

(22) PCT Filed: Feb. 18, 2020

(86) PCT No.: PCT/JP2020/006157
§ 371 (c)(1),
(2) Date: Oct. 8, 2021

(87) PCT Pub. No.: WO2020/208942
PCT Pub. Date: Oct. 15, 2020

(65) Prior Publication Data
US 2022/0160513 A1    May 26, 2022

(30) Foreign Application Priority Data
Apr. 11, 2019   (JP) .................................. 2019-075260

(51) Int. Cl.
*A61F 2/38*    (2006.01)
(52) U.S. Cl.
CPC ............ *A61F 2/389* (2013.01); *A61F 2/3859* (2013.01)

(58) Field of Classification Search
CPC ....................................................... A61F 2/389
See application file for complete search history.

(56) References Cited

U.S. PATENT DOCUMENTS

| 7,413,577 B1 | 8/2008 | Servidio |
| 9,060,866 B2 | 6/2015 | Fankhauser et al. |
| 2003/0153977 A1 | 8/2003 | Suguro et al. |
| 2004/0006394 A1 | 1/2004 | Lipman et al. |
| 2004/0186582 A1 | 9/2004 | Yasuda et al. |

(Continued)

FOREIGN PATENT DOCUMENTS

| AU | 2014250711 A1 | 11/2014 |
| CN | 104970904 A | 10/2015 |

(Continued)

*Primary Examiner* — Megan Y Wolf
(74) *Attorney, Agent, or Firm* — Alleman Hall & Tuttle LLP

(57) ABSTRACT

An artificial knee joint includes: a femoral component including a medial condyle and a lateral condyle; and a tibial component including an inner sliding surface that receives the medial condyle and an outer sliding surface that receives the lateral condyle. A curvature radius of each of the inner sliding surface and the outer sliding surface in a medial-lateral direction increases from an anterior side toward a posterior side within a predetermined range in an anterior-posterior direction. In the medial-lateral direction, the inner sliding surface and the outer sliding surface are positioned inward such that a middle point between a lowest point of the medial condyle and a lowest point of the lateral condyle in a knee extended position is shifted inward relative to a center of the tibial component by 2 to 10% of a width of the tibial component.

4 Claims, 4 Drawing Sheets

MEDIAL ⬅➡ LATERAL

(56) References Cited

U.S. PATENT DOCUMENTS

| | | | |
|---|---|---|---|
| 2012/0095563 A1* | 4/2012 | Sanford | A61F 2/389 |
| | | | 623/20.27 |
| 2013/0129546 A1 | 5/2013 | Kurita et al. | |
| 2013/0197654 A1 | 8/2013 | Samuelson et al. | |
| 2013/0317523 A1 | 11/2013 | Borus | |
| 2014/0277537 A1 | 9/2014 | Todd et al. | |
| 2014/0330388 A1 | 11/2014 | Mizuguchi et al. | |
| 2016/0151162 A1 | 6/2016 | Wyss et al. | |
| 2017/0007415 A1 | 1/2017 | Fiedler et al. | |
| 2018/0206997 A1 | 7/2018 | Sun et al. | |
| 2019/0209331 A1* | 7/2019 | Varadarajan | A61F 2/4261 |

FOREIGN PATENT DOCUMENTS

| | | |
|---|---|---|
| EP | 1174099 A1 | 1/2002 |
| JP | 3781186 B2 | 5/2006 |
| WO | 2012018565 A1 | 2/2012 |
| WO | 2012032350 A2 | 3/2012 |

\* cited by examiner

ARTIFICIAL KNEE JOINT

TECHNICAL FIELD

The present invention relates to an artificial knee joint.

BACKGROUND ART

An artificial knee joint replaces a knee joint of a patient having, for example, knee osteoarthritis, chronic rheumatoid arthritis, osteoma, or an external wound. The artificial knee joint includes a femoral component and a tibial component. The femoral component substitutes for a part of a femur. The tibial component substitutes for a part of a tibia. In some cases, the artificial knee joint includes a patellar component.

In general, the femoral component includes a medial condyle and a lateral condyle, and the tibial component includes an inner sliding surface that receives the medial condyle and an outer sliding surface that receives the lateral condyle (see Patent Literature 1).

CITATION LIST

Patent Literature

PTL 1: Japanese Patent No. 3781186

SUMMARY OF INVENTION

Technical Problem

Although conventional artificial knee joints can realize motion that is similar to the motion of a healthy knee joint, more accurate reproduction of the motion of a healthy knee joint is desired.

In view of the above, an object of the present invention is to provide an artificial knee joint that realizes the same motion as that of a healthy knee joint.

Solution to Problem

In order to solve the above-described problems, the inventors of the present invention conducted diligent studies. As a result, regarding a healthy knee joint, the inventors of the present invention have found that, in a knee extended position, the center of the distal portion (tibia-side end portion) of the femur in the medial-lateral direction is positioned inward relative to the center of the proximal portion (femur-side end portion) of the tibia in the medial-lateral direction. On the other hand, in a conventional artificial knee joint, the center of the femoral component and the center of the tibial component coincide with each other in the medial-lateral direction. In light of this, the inventors of the present invention have come up with the idea that by shifting the center of the femoral component and the center of the tibial component from each other in the medial-lateral direction, the same motion as that of a healthy knee joint can be realized. The present invention has been made from such a point of view.

Specifically, a knee joint of the present invention includes: a femoral component including a medial condyle and a lateral condyle; and a tibial component including an inner sliding surface that receives the medial condyle and an outer sliding surface that receives the lateral condyle, a curvature radius of each of the inner sliding surface and the outer sliding surface in a medial-lateral direction increasing from an anterior side toward a posterior side within a predetermined range in an anterior-posterior direction. In the medial-lateral direction, the inner sliding surface and the outer sliding surface are positioned inward such that a middle point between a lowest point of the medial condyle and a lowest point of the lateral condyle in a knee extended position is shifted inward relative to a center of the tibial component by 2 to 10% of a width of the tibial component.

According to the above configuration, in the medial-lateral direction, in the knee extended position, the relative positional relationship between the femur and the tibia of a patient to whom the artificial knee joint is attached is the same as the relative positional relationship between the femur and the tibia of a healthy person. Regarding a knee flexed position, it has been known that as the knee flexes, the femoral component moves backward. The curvature radius of each of the inner sliding surface and the outer sliding surface in the medial-lateral direction is greater on the posterior side than on the anterior side. Accordingly, when the femoral component moves backward as the knee flexes, restraining force exerted on the femoral component in the medial-lateral direction is reduced. This consequently allows the femoral component to be readily moved in the medial-lateral direction by, for example, the tensile force of soft tissue including the ligaments and the joint capsule. Specifically, even when flexing the knee, the relative positional relationship between the femur and the tibia of the patient to whom the artificial knee joint is attached would be the same as the relative positional relationship between the femur and the tibia of a healthy person. Therefore, the balance between the tension and relaxation of soft tissue when the artificial knee joint is attached is similar to the balance between the tension and relaxation of soft tissue of a healthy knee joint. This makes it possible to realize the same motion as that of a healthy knee joint.

In the anterior-posterior direction, a contact position where the medial condyle and the inner sliding surface contact each other in the knee extended position may be within a range of 40 to 65% of a length of the tibial component from a posterior end of the tibial component. According to this configuration, also in the anterior-posterior direction, the relative positional relationship between the femur and the tibia of the patient to whom the artificial knee joint is attached is the same as the relative positional relationship between the femur and the tibia of a healthy person.

An inclined surface that is inclined outward and downward may be formed on an end portion of an upper surface of the tibial component, the end portion protruding outward relative to the femoral component. According to this configuration, interference between the lateral collateral ligament and the tibial component can be avoided.

A lowest point line formed by lowest points of the inner sliding surface in the medial-lateral direction, the lowest points being continuously arranged in the anterior-posterior direction, may curve inward while extending forward. According to this configuration, when flexing the knee, the femoral component can be guided outward as the femoral component moves backward.

Advantageous Effects of Invention

The present invention makes it possible to realize the same motion as that of a healthy knee joint.

DESCRIPTION OF EMBODIMENTS

Figure 1:
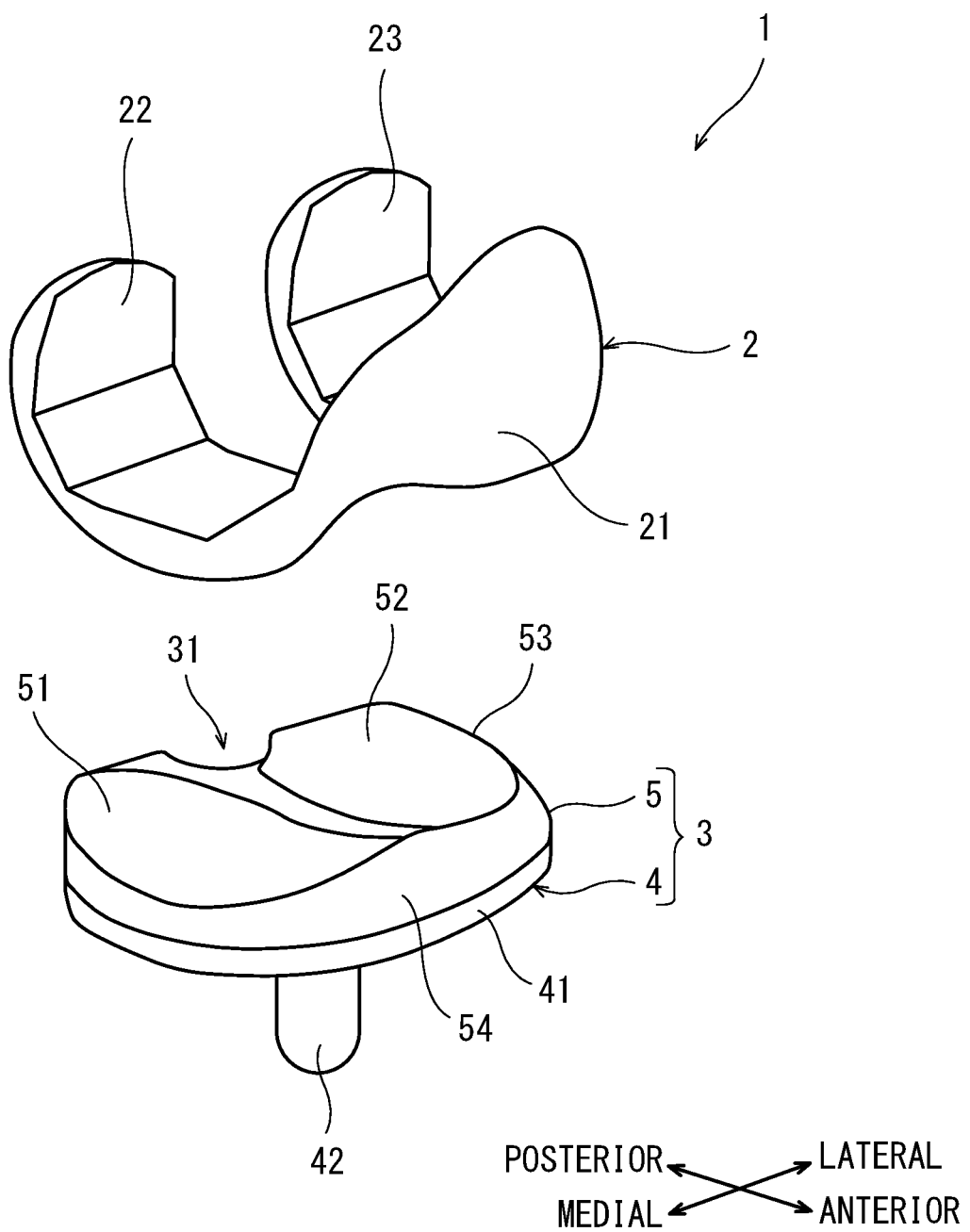
FIG. 1 is an exploded perspective view of an artificial knee joint according to one embodiment of the present invention.
Figure 2:
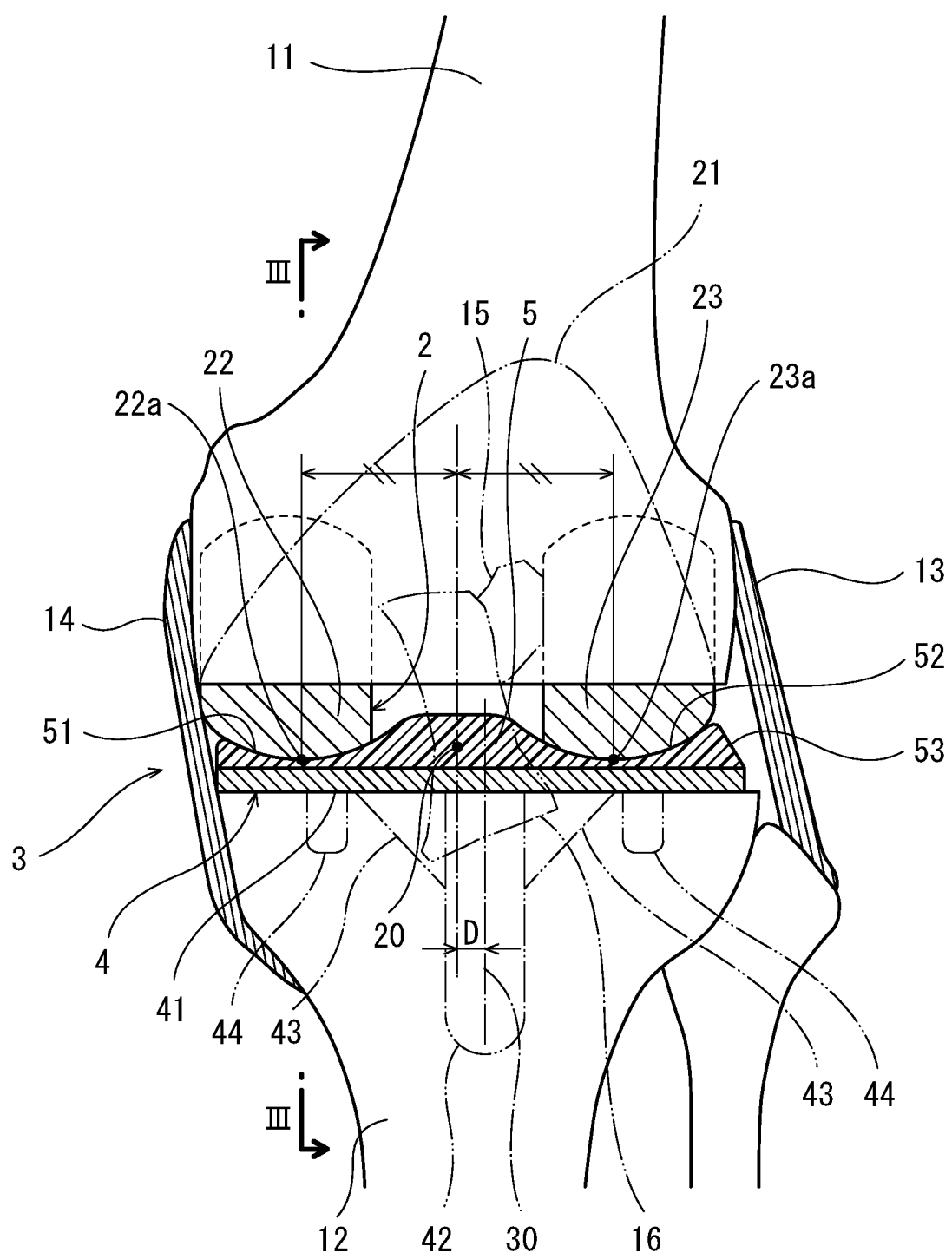
FIG. 2 is a sectional view showing an attached state of the artificial knee joint of FIG. 1.

FIG. 1 shows an artificial knee joint 1 according to one embodiment of the present invention. The artificial knee joint 1 of the present embodiment is intended for a left leg. In FIG. 1, the direction toward the lower left is the medial direction; the direction toward the upper right is the lateral direction; the direction toward the lower right is the anterior direction; and the direction toward the upper left is the posterior direction. FIG. 2 is a sectional view showing an attached state of the artificial knee joint 1.

The artificial knee joint 1 includes a femoral component 2 and a tibial component 3. The femoral component 2 substitutes for a resected part of a femur 11. The tibial component 3 substitutes for a resected part of a tibia 12. It should be noted that, in FIG. 2, reference sign 13 indicates a lateral collateral ligament; reference sign 14 indicates a medial collateral ligament; reference sign 15 indicates an anterior cruciate ligament; and reference sign 16 indicates a posterior cruciate ligament.

The femoral component 2 is made of metal, such as a cobalt-chromium alloy or a titanium alloy. The femoral component 2 includes an anterior wall 21, a medial condyle 22, and a lateral condyle 23. The anterior wall 21 is fixed to an anterior resection surface of the femur 11. Each of the medial condyle 22 and the lateral condyle 23 extends from the lower end of the anterior wall 21 to the posterior side of the femur 11 in a manner to pass under the femur 11.

The medial condyle 22 and the lateral condyle 23 are spaced apart from each other in the medial-lateral direction. The gap between the medial condyle 22 and the lateral condyle 23 is intended for avoiding interference with the anterior cruciate ligament 15 and the posterior cruciate ligament 16. A patella groove, on which the patella or a patellar component slides, is formed in the lower portion of the anterior wall 21, such that the patella groove extends in the anterior-posterior direction that passes between the medial condyle 22 and the lateral condyle 23.

The external surface of the medial condyle 22 is a three-dimensional curved surface that is curved in the anterior-posterior direction and the medial-lateral direction. Similarly, the external surface of the lateral condyle 23 is also a three-dimensional curved surface that is curved in the anterior-posterior direction and the medial-lateral direction.

In the present embodiment, the tibial component 3 is of a type that is used in a case where the anterior cruciate ligament 15 is resected, but the posterior cruciate ligament 16 is preserved. Alternatively, the tibial component 3 may be of a type that is used in a case where both the anterior cruciate ligament 15 and the posterior cruciate ligament 16 are resected. When the tibial component 3 is of a type that is used in a case where both the anterior cruciate ligament 15 and the posterior cruciate ligament 16 are resected, the tibial component 3 includes an upward projection that is formed on substantially the center of the tibial component 3. Further alternatively, the tibial component 3 may be of a type that is used in a case where both the anterior cruciate ligament 15 and the posterior cruciate ligament 16 are preserved, or may be of a type that is used in a case where the posterior cruciate ligament 16 is preserved and the anterior cruciate ligament 15 is reconstructed.

The tibial component 3 includes a base 4 and a resin plate 5. The base 4 is made of metal such as a cobalt-chromium alloy or a titanium alloy. The resin plate 5 is made of, for example, polyethylene. The base 4 includes a plate portion 41 and a stem 42. The plate portion 41 is fixed to an upper resection surface of the tibia 12. The stem 42 extends downward from substantially the center of the plate portion 41. The base 4 further includes triangular keels 43, which are connected to the plate portion 41 and the stem 42. The base 4 may include, in addition to or instead of the stem 42 and the keels 43, a pair of pegs 44 positioned below an inner sliding surface 51 and an outer sliding surface 52. The inner sliding surface 51 and the outer sliding surface 52 will be described below.

As seen in a plan view, the contour shape of the resin plate 5 is the same as the contour shape of the plate portion 41 of the base 4. The inner sliding surface 51, which receives the medial condyle 22 of the femoral component 2, and the outer sliding surface 52, which receives the lateral condyle 23 of the femoral component 2, are formed on the upper surface of the resin plate 5.

The inner sliding surface 51 is a three-dimensional curved surface that is curved in the anterior-posterior direction and the medial-lateral direction. Similarly, the outer sliding surface 52 is also a three-dimensional curved surface that is curved in the anterior-posterior direction and the medial-lateral direction.

Figure 4:
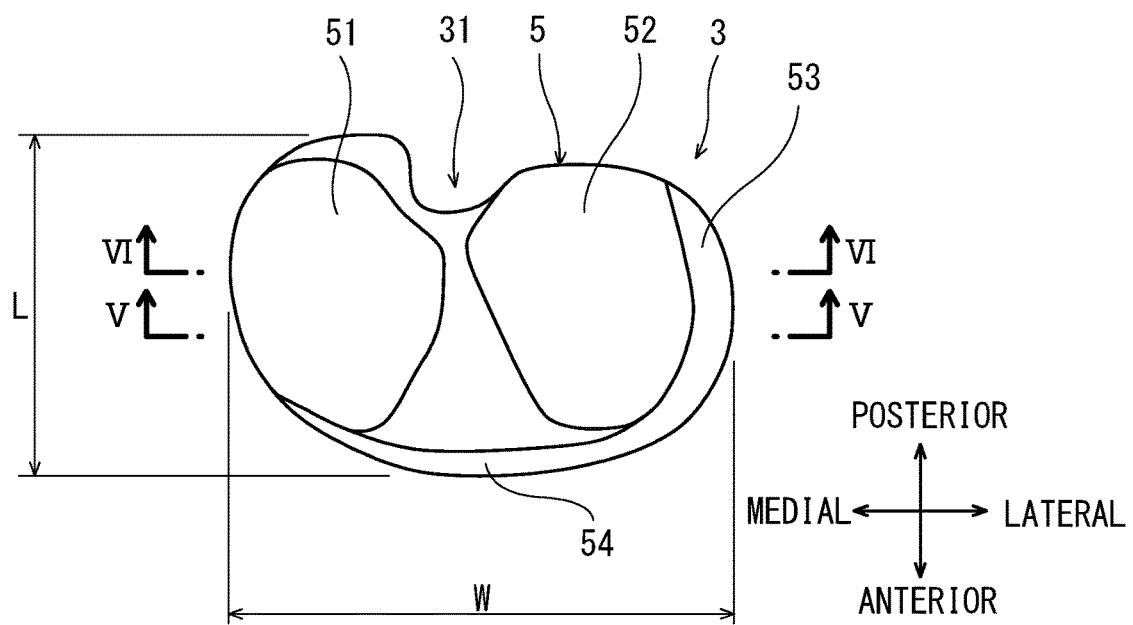
FIG. 4 is a plan view of a tibial component.
Figure 5:
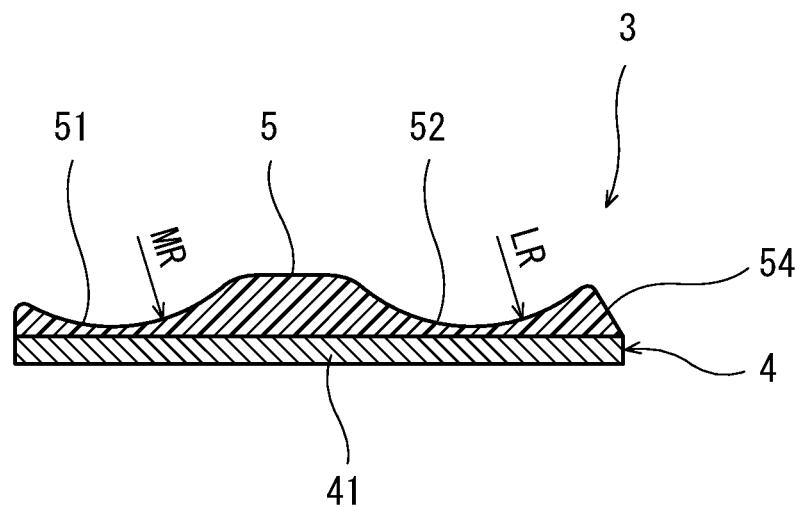
FIG. 5 is a sectional view taken along line V-V of FIG. 4.
Figure 6:
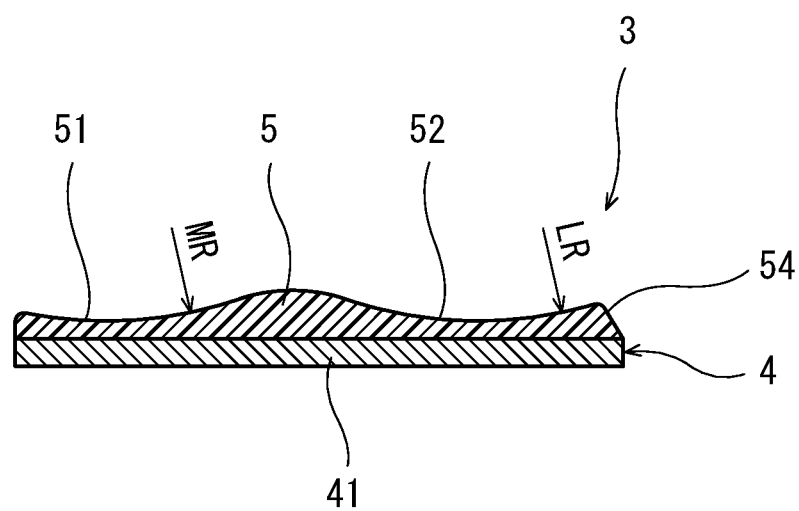
FIG. 6 is a sectional view taken along line VI-VI of FIG. 4.

To be more specific, as shown in FIGS. 4 to 6, the curvature radius MR of the inner sliding surface 51 in the medial-lateral direction increases from the anterior side toward the posterior side within a predetermined range in the anterior-posterior direction. For example, the predetermined range is a middle region in a case where the inner sliding surface 51 is trisected in the anterior-posterior direction.

Similarly, the curvature radius LR of the outer sliding surface 52 in the medial-lateral direction increases from the anterior side toward the posterior side within a predetermined range in the anterior-posterior direction. For example, the predetermined range is a middle region in a case where the outer sliding surface 52 is trisected in the anterior-posterior direction.

The inner sliding surface 51 and the outer sliding surface 52 are not provided at bilateral symmetrical positions, but they are positioned inward. To be more specific, as shown in FIG. 2, in the medial-lateral direction, the inner sliding surface 51 and the outer sliding surface 52 are positioned inward such that a middle point 20 between a lowest point 22a of the medial condyle 22 and a lowest point 23a of the lateral condyle 23 in a knee extended position is shifted inward relative to a center 30 of the tibial component 3 by 2 to 10% of a width W of the tibial component 3 (see FIG. 4). In other words, a distance D between the middle point 20 and the center 30 of the tibial component 3 in the medial-lateral direction is not less than 0.02×W and not greater than 0.1×W. It should be noted that the center 30 of the tibial component 3 in the medial-lateral direction is a line that bisects the width W of the tibial component 3 in the medial-lateral direction.

Figure 3:
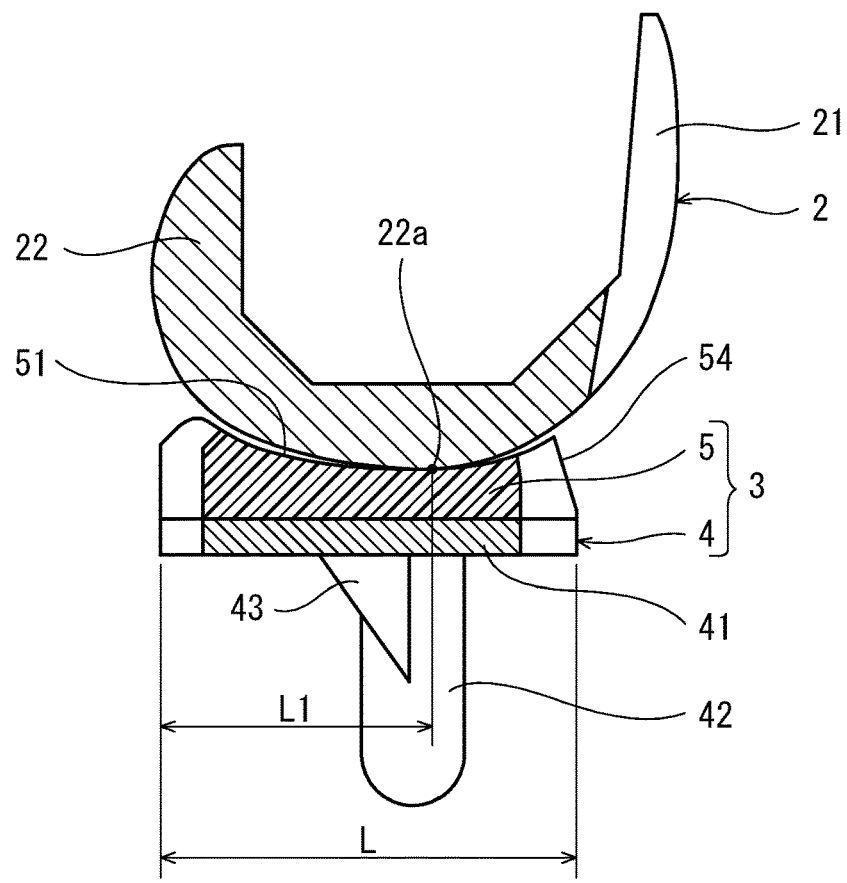
FIG. 3 is a sectional view taken along line of FIG. 2 (the illustration of a femur and a tibia is omitted).

Further, as shown in FIG. 3, in the anterior-posterior direction, a contact position where the medial condyle 22 and the inner sliding surface 51 contact each other in the knee extended position (the contact position is also the lowest point 22a of the medial condyle 22) is within a range of 40 to 65% of a length L of the tibial component 3 from the posterior end of the tibial component 3. In other words, a distance L1 from the posterior end of the tibial component 3 to the contact position is not less than 0.4×L and not greater than 0.65×L.

Further, as shown in FIG. 2 and FIG. 4, an inclined surface 53, which is inclined outward and downward, is formed on an end portion of the upper surface of the resin plate 5 (the upper surface of the tibial component 3), the end portion protruding outward relative to the femoral component 2. In present embodiment, the outer sliding surface 52 and the inclined surface 53 are adjacent to each other, and the boundary therebetween forms a ridge.

As shown in FIG. 3 and FIG. 4, also on the anterior end portion of the upper surface of the resin plate 5, an inclined surface 54 is formed, which is inclined forward and downward.

The tibial component 3 is further provided with a recess 31 for avoiding interference with the posterior cruciate ligament 16. The recess 31 is recessed forward from the posterior end of the tibial component 3. That is, a notch having the same shape as that of the recess 31 is formed in both the plate portion 41 of the base 4 and the resin plate 5. Similar to the inner sliding surface 51 and the outer sliding surface 52 being positioned inward, the recess 31 is positioned inward relative to the center 30 of the tibial component 3 in the medial-lateral direction.

As described above, in the artificial knee joint 1 of the present embodiment, the inner sliding surface 51 and the outer sliding surface 52 of the tibial component 3 are positioned inward. Accordingly, in the medial-lateral direction, in the knee extended position, the relative positional relationship between the femur 11 and the tibia 12 of a patient to whom the artificial knee joint 1 is attached is the same as the relative positional relationship between the femur and the tibia of a healthy person. Regarding a knee flexed position, it has been known that as the knee flexes, the femoral component 2 moves backward. The curvature radius MR of the inner sliding surface 51 and the curvature radius LR of the outer sliding surface 52 in the medial-lateral direction are greater on the posterior side than on the anterior side. Accordingly, when the femoral component 2 moves backward as the knee flexes, restraining force exerted on the femoral component 2 in the medial-lateral direction is reduced. This consequently allows the femoral component 2 to be readily moved in the medial-lateral direction by, for example, the tensile force of soft tissue including the ligaments and the joint capsule. Specifically, even when flexing the knee, the relative positional relationship between the femur 11 and the tibia 12 of the patient to whom the artificial knee joint 1 is attached would be the same as the relative positional relationship between the femur and the tibia of a healthy person. Therefore, the balance between the tension and relaxation of soft tissue when the artificial knee joint 1 is attached is similar to the balance between the tension and relaxation of soft tissue of a healthy knee joint. This makes it possible to realize the same motion as that of a healthy knee joint.

Further, in the present embodiment, the contact position where the medial condyle 22 and the inner sliding surface 51 contact each other in the knee extended position is within the range of 40 to 65% of the length L of the tibial component 3 from the posterior end of the tibial component 3. Accordingly, also in the anterior-posterior direction, the relative positional relationship between the femur 11 and the tibia 12 of the patient to whom the artificial knee joint 1 is attached is the same as the relative positional relationship between the femur and the tibia of a healthy person.

In addition, since the inclined surface 53 is formed on the outer end portion of the upper surface of the tibial component 3, interference between the lateral collateral ligament 13 and the tibial component 3 can be avoided.

(Variations)

The present invention is not limited to the above-described embodiment. Various modifications can be made without departing from the scope of the present invention.

For example, the artificial knee joint 1 may include a patellar component in addition to the femoral component 2 and the tibial component 3.

Further, the inner sliding surface 51 of the tibial component 3 may be configured such that a lowest point line formed by lowest points of the inner sliding surface 51 in the medial-lateral direction, the lowest points being continuously arranged in the anterior-posterior direction, curves inward (i.e., opposite the outer sliding surface 52) while extending forward. According to this configuration, when flexing the knee, the femoral component 2 can be guided outward as the femoral component 2 moves backward.

When the tibial component 3 is of a type that is used in a case where both the anterior cruciate ligament 15 and the posterior cruciate ligament 16 are preserved, the tibial component 3 is substantially U-shaped as seen in a plan view, i.e., a groove whose opening faces backward is formed between the inner sliding surface 51 and the outer sliding surface 52. In this case, the stem 42 and the keels 43 are eliminated.

REFERENCE CHARACTERS LIST 1 artificial knee joint
2 femoral component
20 middle point
22 medial condyle
22a lowest point
23 lateral condyle
23a lowest point
3 tibial component
30 center
51 inner sliding surface
52 outer sliding surface
54 inclined surface

The invention claimed is:

1. An artificial knee joint comprising:
a femoral component including a medial condyle and a lateral condyle; and
a tibial component including an inner sliding surface that receives the medial condyle and an outer sliding surface that receives the lateral condyle, a curvature radius of each of the inner sliding surface and the outer sliding surface in a medial-lateral direction increasing from an anterior side toward a posterior side within a predetermined range in an anterior-posterior direction, wherein
in the medial-lateral direction, the inner sliding surface and the outer sliding surface are positioned inward such that a middle point between a lowest point of the medial condyle and a lowest point of the lateral condyle in a knee extended position is shifted inward relative to a center of the tibial component by 2 to 10% of a width of the tibial component.

2. The artificial knee joint of claim 1, wherein
in the anterior-posterior direction, a contact position where the medial condyle and the inner sliding surface contact each other in the knee extended position is within a range of 40 to 65% of a length of the tibial component from a posterior end of the tibial component.

3. The artificial knee joint according to claim 1, wherein an inclined surface that is inclined outward and downward is formed on an end portion of an upper surface of the tibial component, the end portion protruding outward relative to the femoral component.

4. The artificial knee joint according to claim 1, wherein a lowest point line formed by lowest points of the inner sliding surface in the medial-lateral direction, the lowest points being continuously arranged in the anterior-posterior direction, curves inward while extending forward.

* * * * *